United States Patent [19]

Kleemann et al.

[11] 4,342,874
[45] Aug. 3, 1982

[54] 2-[2'-(HYDANTO-5-YL)-ETHYL]-5,5-DIMETHYL-1,3-DIOXANE

[75] Inventors: Axel Kleemann; Marc Samson, both of Hanau, Fed. Rep. of Germany

[73] Assignee: Degussa Aktiengesellschaft, Frankfurt, Fed. Rep. of Germany

[21] Appl. No.: 320,130

[22] Filed: Nov. 10, 1981

[30] Foreign Application Priority Data

Nov. 15, 1980 [DE] Fed. Rep. of Germany ....... 3043250

[51] Int. Cl.³ ............................................ C07D 405/06
[52] U.S. Cl. ..................................................... 548/309
[58] Field of Search ......................................... 548/309

[56] References Cited

U.S. PATENT DOCUMENTS 2,557,904 6/1951 Britton et al. ........................ 548/309

Primary Examiner—Robert W. Ramsuer

Attorney, Agent, or Firm—Cushman, Darby & Cushman

[57] ABSTRACT

The invention is directed to 2-[2'-(hydanto-5-yl)-ethyl]-5,5-dimethyl-1,3-dioxane of the formula

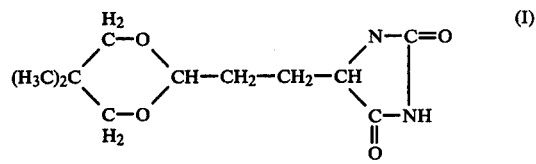

its production by reaction of 2-(2'-formylethyl)-5,5-dimethyl-1,3-dioxane with hydrogen cyanide or a cyanide ion supplying compound, ammonia, or an ammonium ion supplying compound and carbon dioxide or a carbonate ion supplying compound in aqueous alcoholic solution and its use for the production of tryptophane-hydantoin.

1 Claim, No Drawings

2-[2'-(HYDANTO-5-YL)-ETHYL]-5,5-DIMETHYL-1,3-DIOXANE

SUMMARY OF THE INVENTION

The invention is directed to 2-[2'-(hydanto-5-yl)-ethyl]-5,5-dimethyl-1,3-dioxane of the formula

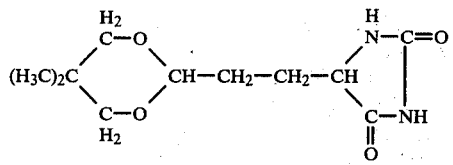

and a process for its production.

2-[2'-(hydanto-5-yl)-ethyl]-5,5-dimethyl-1,3-dioxane is a valuable intermediate product for the production of tryptophane-hydantoin. A further object of the invention therefore is the use of compound (I) to produce tryptophane-hydantoin.

Tryptophane is an essential aminoacid which frequenctly represents the limiting agent in fodders and mixed fodders. Since tryptophane can be obtained through alkaline hydrolysis of tryptophane-hydantoin, its synthesis is of great significance.

There are already known a number of processes for the production of tryptophane-hydantoin, the most recent of which start from either acrolein or acrylonitrile and proceed via several steps. The known processes, however, are not completely satisfactory because they either require the use of reactants or assistants which are difficult to obtain or involve at least one reaction step having only relatively low yields.

2-[2'-(hydanto-5-yl)-ethyl]-5,5-dimethyl-1,3-dioxane can be produced in a simple manner and with good yield by reacting 2-(2'-formylethyl)-5,5-dimethyl-1,3-dioxane of the formula

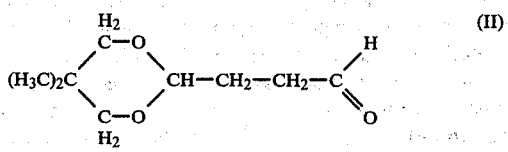

in aqueous or aqueous-alcoholic solution with hydrogen cyanide or a cyanide ion supplying compound, ammonia or an ammonium ion supplying compound and carbon dioxide or a carbonate ion supplying compound.

The 2-(2'-formylethyl)-5,5-dimethyl-1,3-dioxane employed as starting material can likewise be obtained easily with high yield through hydroformylation of 2-vinyl-5,5-dimethyl-1,3-dioxane, which in turn is easily obtainable by reaction of acrolein with 2,2-dimethyl-propanediol-1,3.

On the other hand 2-[2'-(hydanto-5-yl)-ethyl]-5,5-dimethyl-1,3-dioxane in the presence of acids by reaction with phenylhydrazine is readily converted into tryptophane-hydantoin with good yield. Therefore it represents a key product in a new process for the production of tryptophane-hydantoin and tryptophane itself starting from acrolein.

To produce 2-[2'-(hydanto-5-yl)-ethyl]-5,5-dimethyl-1,3-dioxane, 2-(2'-formylethyl)-5,5-dimethyl-1,3-dioxane is reacted in a manner which is known in itself for the formation of hydantoins from aldehydes with hydrogen cyanide or a cyanide ion supplying compound, such as sodium cyanide or potassium cyanide, with ammonia or an ammonium ion supplying compound, such as ammonium hydroxide or ammonium chloride, and with carbon dioxide or a carbonate ion supplying compound, such as sodium or potassium bicarbonate, sodium or potassium carbonate or sodium or potassium, carbamate. There can also be employed compounds which simultaneously supply cyanide and ammonium ions such as ammonium cyanide, or compounds which simultaneously supply ammonia and carbonate ions, such as ammonium carbonate or ammonium carbamate.

The reaction takes place in water or in a mixture of water and methanol or ethanol. It can be undertaken in a wide temperature range. Preferably there is employed a temperature between 35° and 90° C., because in this range a satisfactory reaction speed is attained and the perhaps necessary superatmospheric pressure does not create an industrial obstacle.

The amount of the individual reactants can be varied within a wide range. Preferably per mole of 2-(2'-formylethyl)-5,5-dimethyl-1,3-dioxane there is employed 1 to 1.5 moles of hydrogen cyanide or cyanide ion supplying compound, 2 to 15 moles of ammonia or an ammonium ion supplying compound and 1 to 2 moles of carbon dioxide or a carbonate ion supplying compound. The 2-(2'-formylethyl)-5,5-dimethyl-1,3-dioxane can be reacted simultaneously with all three other reactants. However, it is likewise also possible to first react it with the cyanide component to form the corresponding cyanohydrin and subsequently react this simultaneously with the two other components, or first to react the cyanohydrin only with the ammonium component and only after that react with the carbon dioxide or carbonate component. It is especially advantageous to have the 2-(2'-formylethyl)-5,5-dimethyl-1,3-dioxane dissolved in methanol or ethanol and to slowly feed this solution into an aqueous solution or suspension of the other reactants at the desired reaction temperature. For obtaining a high conversion there is recommended a suitable post reaction time of, for example, about 5 hours after the end of the feeding in.

Since the 2-[2'-(hydanto-5-yl)-ethyl]-5,5-dimethyl-1,3-dioxane formed is only slightly soluble in water at low temperatures, after distillation of the alcohol, it can be separated practically completely and in high purity by cooling the reaction mixture to a temperature below 25° C.

After the separation of the 2-[2'-(hydanto-5-yl)-ethyl]-5,5-dimethyl-1,3-dioxane the mother liquor remaining still contains dissolved therein, in certain cases, a certain amount of α-N-carbamoyl-carboxylic acid amide of the formula

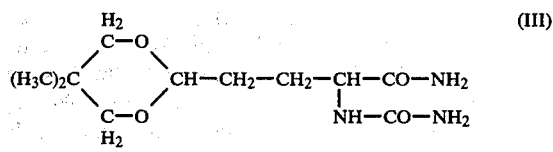

formed as byproduct. This compound can easily be transformed in the hydantoin at a pH below 7. Alternatively, the mother liquor, after concentrating when necessary can be recycled in the process without any difficulty.

In order to produce tryptophane-hydantoin from the 2-[2'-(hydanto-5-yl)-ethyl]-5,5-dimethyl-1,3-dioxane it is reacted at a pH between 0.1 and 4, preferably between 1 and 3 with phenylhydrazine. The required pH can be established by an inorganic acid such as sulfuric acid or phosphoric acid, through an organic acid such as oxalic acid, formic acid, acetic acid, benzene sulfonic acid, or p-toluenesulfonic acid or by a strongly acid ion exchanger, e.g., a sulfonated styrene-divinyl benzene resin. Preferably there is used hydrochloric acid. Since in the formation of tryptophane-hydantoin from 2-[2'-(hydanto-5-yl)-ethyl]-5,5-dimethyl-1,3-dioxane there is set free per mole one mole of ammonia, in certain cases it is necessary to regulate the pH by addition of acid. The reaction temperature can be varied within wide limits. Suitable are temperatures between 60° and 150° C., preferably between 70° and 120° C.

The phenylhydrazine can be employed in excess. However, for economical reasons it is more advantageous to only use the amount which is equivalent to the 2-[2'-(hydanto-5-yl)-ethyl]-5,5-dimethyl-1,3-dioxane.

The phenyldrazine can be mixed with the 2-[2'-(hydanto-5-yl)-ethyl]-5,5-dimethyl-1,3-dioxane and the necessary amount of acid and be heated to the desired reaction temperature. However, it is likewise also possible to have present an acid solution of the phenylhydrazine, to heat, and feed in a solution of 2-[2'-(hydanto-5-yl)-ethyl]-5,5-dimethyl-1,3-dioxane. In both cases a reaction time in all of 3 to 4 hours is generally sufficient. After the end of the reaction the solution of tryptophane-hydantoin obtained can be concentrated and the residue recrystallised. However, the tryptophane-hydantoin can also be crystallized and separated through cooling of the solution. The purity of the product thus obtained normally is over 95%. By recrystallization there is obtained a pure tryptophane-hydantoin having a melting point of 213° to 216° C.

The invention is explained further in the following examples. Unless otherwise indicated all percentages are by weight.

The process can comprise, consist essentially of, or consist of the stated steps with the recited materials.

DETAILED DESCRIPTION

EXAMPLE 1

There were introduced into a flask equipped with a stirrer and reflux condenser 1090 grams of aqueous ammonia (25%), 288 grams of ammonium carbonate, 180 grams of water and 95 ml of liquid hydrogen cyanide. The mixture was heated to 40° C. At this temperature there were added within one hour 344 grams of 2-(2'-formylethyl)-5,5-dimethyl-1,3-dioxane dissolved in 500 ml of methanol, after which the temperature was held at 40° C. for a further 5 hours. Subsequently the methanol was distilled off and through further heating to 100° C. the ammonium salts were boiled out. During slow cooling to 20° C., 388 grams of 2-[2'-(hydanto-5-yl)-ethyl]-5,5-dimethyl-1,3-dioxane (80% of theory) crystallized out. Melting point: 168°–171° C.

Elemental Analysis $C_{11}H_{18}N_2O_4$

Calculated: C: 54,53%; H: 7,49%; N: 11,56%; Found: C: 54,18%; H: 7,30%; N: 11,81%.

IR-Spectrum: 3500–3000 cm$^{-1}$; 1785 cm$^{-1}$; 1740 cm$^{-1}$ $^1$H-NMR-Spectrum: (DMSO d6-CDCl$_3$):

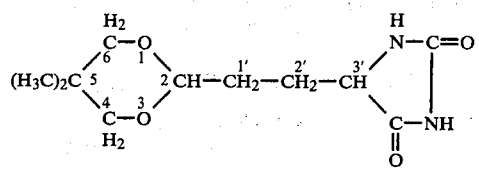

$\delta = 0{,}70$ (s, 3H): 5—CH$_3$
$\delta = 1{,}10$ (s, 3H): 5—CH$_3$
$\delta = 1{,}3$–1,9 (m, 4H): H-1', H-2'
$\delta = 3{,}4$ (q, 4H): H-4, H-6
$\delta = 3{,}95$ (m, 1H): H-3
$\delta = 4{,}5$ (t, 1H): H-2
$\delta = 7{,}9$ (s, 1H): NH
$\delta = 10{,}5$ (s, 1H): NH

EXAMPLE 2

There were introduced into an autoclave equipped with a stirrer 680 grams of aqueous ammonia (25%), 288 grams of ammonium carbonate and 390 ml of water. Subsequently there were added with stirring 116 ml of hydrogen cyanide. Then there was added with stirring at a temperature of about 35° C. within one hour a solution of 344 grams of 2-(2'-formylethyl)-5,5-dimethyl-1,3-dioxane in 500 ml of methanol. The mixture was held for 3 hours at 70° C. Then the methanol was distilled off and the ammonium salts boiled off through further heating at 100° C. During slow cooling to room temperature there crystallized out 411 grams (85% of theory) of 2[2'-(hydanto-5-yl)-ethyl]-5,5-dimethyl-1,3-dioxane. Melting point: 169°–171° C.

EXAMPLE 3

In the course of one hour there was dropped into a solution of 26 grams of potassium cyanide in 150 ml of water a solution of 68.8 grams of 2-(2'-formylethyl)-5,5-dimethyl-1,3-dioxane in 150 ml of methanol and the mixture was stirred for one more hour at 25° C. Subsequently the reaction mixture in the course of one hour at 35° to 40° C. was dropped into a stirred suspension of 76.8 grams of ammonium carbonate and 200 ml of aqueous ammonia (25%) and the mixture was stirred for a further 5 hours at 40° C. Then the methanol was distilled off, the ammonium salts were boiled out and the reaction mixture was concentrated at 100° C. to 180 ml total volume. During cooling to room temperature there crystallized out 81.3 grams (84% of theory) of 2-[2'-(hydanto-5-yl)-ethyl]-5,5-dimethyl-1,3-dioxane.

EXAMPLE 4

A solution of 24.2 grams of 2-[2'-(hydanto-5-yl)-ethyl]-5,5-dimethyl-1,3-dioxane produced according to one of Examples 1 to 3 in 250 ml of 0.1 N HCl heated to 80° C. was dropped within 1 hour into a stirred solution of 9.9 grams of phenylhydrazine in 100 ml of 0.1 N HCl heated to 90° C. The reaction mixture was subsequently held for a further 2.5 hours at 90° C. After slow cooling to 10° C. the precipitate formed was filtered off, washed with water and dried at reduced pressure. The yield of tryptophane-hydantoin was 18.9 grams (82.5% of theory).

Elemental Analysis $C_{12}H_{11}N_3O_2$

Calculated: C: 62,9%; H: 4,8%; N: 18,3%; Found: C: 61,6%; H: 4,9%; N: 18,1%.

EXAMPLE 5

A suspension of 96.8 grams of 2-[2'-(hydanto-5-yl)-ethyl]-5,5-dimethyl-1,3-dioxane, 57.8 grams of phenylhydrazine hydrochloride, 50 ml of 2 N HCL and 1200 ml of water was heated for 3 hours under vigorous stirring at 90° C. After slowly cooling to 10° C. the precipitate formed was filtered off and dried at reduced pressure. The yield of tryptophane-hydantoin was 75.5 grams (78% of theory).

What is claimed is:

1. 2-[2'-(hydanto-5-yl)-ethyl]-5,5-dimethyl-1,3-dioxane of the formula

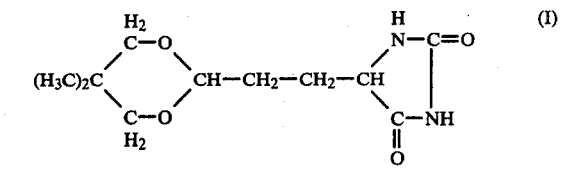

* * * * *